(12) United States Patent  
Lisseman et al.

(10) Patent No.: US 8,725,230 B2  
(45) Date of Patent: May 13, 2014

(54) STEERING WHEEL WITH HAND SENSORS

(75) Inventors: Jason Lisseman, Shelby Township, MI (US); Tom Mogg, Shelby Township, MI (US)

(73) Assignee: TK Holdings Inc., Auburn Hills, MI (US)

( * ) Notice: Subject to any disclaimer, the term of this patent is extended or adjusted under 35 U.S.C. 154(b) by 286 days.

(21) Appl. No.: 13/078,799

(22) Filed: Apr. 1, 2011

(65) Prior Publication Data  
US 2011/0245643 A1 Oct. 6, 2011

Related U.S. Application Data

(60) Provisional application No. 61/320,591, filed on Apr. 2, 2010.

(51) Int. Cl.
| | |
|---|---|
| *A61B 5/0408* | (2006.01) |
| *A61B 5/01* | (2006.01) |
| *A61B 5/053* | (2006.01) |
| *B60K 28/00* | (2006.01) |
| *G08B 23/00* | (2006.01) |

(52) U.S. Cl.  
USPC ........... 600/393; 600/372; 600/509; 600/547; 600/549; 180/272; 340/576

(58) Field of Classification Search  
USPC .................. 600/393, 372, 509, 547; 340/576; 180/272  
See application file for complete search history.

(56) References Cited

U.S. PATENT DOCUMENTS

| | | | | |
|---|---|---|---|---|
| 3,731,672 | A | * | 5/1973 | McIntosh ....................... 600/516 |
| 4,268,815 | A | | 5/1981 | Eventoff et al. |
| 4,276,538 | A | | 6/1981 | Eventoff et al. |
| 4,301,337 | A | | 11/1981 | Eventoff |
| 4,314,227 | A | | 2/1982 | Eventoff |
| 4,314,228 | A | | 2/1982 | Eventoff |
| 4,315,238 | A | | 2/1982 | Eventoff |
| 4,319,581 | A | * | 3/1982 | Cutter ........................... 600/520 |
| 4,451,714 | A | | 5/1984 | Eventoff |
| 4,489,302 | A | | 12/1984 | Eventoff |
| 4,572,207 | A | * | 2/1986 | Yoshimi et al. ............... 600/519 |
| 4,739,299 | A | | 4/1988 | Eventoff et al. |
| 4,810,992 | A | | 3/1989 | Eventoff |
| 4,963,702 | A | | 10/1990 | Yaniger et al. |
| 5,053,585 | A | | 10/1991 | Yaniger |
| 5,159,159 | A | | 10/1992 | Asher |
| 5,186,055 | A | | 2/1993 | Kovacich et al. |
| 5,209,967 | A | | 5/1993 | Wright et al. |
| 5,262,778 | A | | 11/1993 | Saunders |

(Continued)

FOREIGN PATENT DOCUMENTS

| | | |
|---|---|---|
| DE | 60011078 T2 | 6/2005 |
| DE | 60210951 T2 | 1/2007 |

(Continued)

*Primary Examiner* — Lee S Cohen  
(74) *Attorney, Agent, or Firm* — Meunier Carlin & Curfman, LLC

(57) ABSTRACT

The invention relates to a steering wheel for a vehicle can include a sensor assembly mounted in the steering wheel. The sensor assembly can include an electrode configured to measure a biological parameter of a driver of the vehicle. In invention further relates to a sensor assembly for a steering wheel. The sensor assembly can include an electrode configured to measure a biological parameter of a driver of the vehicle. The sensor assembly can be configured to be mounted in the steering wheel.

20 Claims, 3 Drawing Sheets

(56) References Cited

U.S. PATENT DOCUMENTS

| | | | |
|---|---|---|---|
| 5,296,837 | A | 3/1994 | Yaniger |
| 5,302,936 | A | 4/1994 | Yaniger |
| 5,365,671 | A | 11/1994 | Yaniger |
| 5,510,783 | A | 4/1996 | Findlater et al. |
| 5,659,334 | A | 8/1997 | Yaniger et al. |
| 5,670,988 | A | 9/1997 | Tickle |
| 5,828,363 | A | 10/1998 | Yaniger et al. |
| 5,847,639 | A | 12/1998 | Yaniger |
| 5,854,625 | A | 12/1998 | Frisch et al. |
| 5,907,419 | A | 5/1999 | Martnelli et al. |
| 5,943,044 | A | 8/1999 | Martinelli et al. |
| 5,982,519 | A | 11/1999 | Martnelli et al. |
| 6,084,572 | A | 7/2000 | Yaniger |
| 6,104,296 | A * | 8/2000 | Yasushi et al. ............... 340/576 |
| 6,165,129 | A * | 12/2000 | Bates ........................... 600/481 |
| 6,239,707 | B1 * | 5/2001 | Park ............................. 340/576 |
| 6,239,790 | B1 | 5/2001 | Martinelli et al. |
| 6,291,568 | B1 | 9/2001 | Lussey |
| 6,388,556 | B1 | 5/2002 | Imai et al. |
| 6,396,523 | B1 | 5/2002 | Segal et al. |
| 6,429,846 | B2 | 8/2002 | Rosenberg et al. |
| 6,437,682 | B1 | 8/2002 | Vance |
| 6,495,069 | B1 | 12/2002 | Lussey et al. |
| 6,529,122 | B1 | 3/2003 | Magnussen et al. |
| 6,531,951 | B2 | 3/2003 | Serban et al. |
| 6,538,643 | B2 | 3/2003 | Mori et al. |
| 6,563,415 | B2 | 5/2003 | Armstrong |
| 6,646,540 | B1 | 11/2003 | Lussey |
| 6,690,365 | B2 | 2/2004 | Hinckley et al. |
| 6,750,803 | B2 | 6/2004 | Yates et al. |
| 6,758,689 | B1 | 7/2004 | Bair et al. |
| 6,765,557 | B1 | 7/2004 | Segal et al. |
| 6,791,532 | B2 | 9/2004 | Hirano et al. |
| 6,801,191 | B2 | 10/2004 | Mukai et al. |
| 6,809,280 | B2 | 10/2004 | Divigalpitiya et al. |
| 6,820,804 | B2 | 11/2004 | Segal et al. |
| 6,822,640 | B2 | 11/2004 | Derocher |
| 6,850,221 | B1 | 2/2005 | Tickle |
| 6,861,961 | B2 | 3/2005 | Sandbach et al. |
| 6,875,938 | B2 | 4/2005 | Schmiz et al. |
| 6,888,537 | B2 | 5/2005 | Benson et al. |
| 6,909,354 | B2 | 6/2005 | Baker et al. |
| 6,947,031 | B2 | 9/2005 | Sandbach et al. |
| 6,995,752 | B2 | 2/2006 | Lu |
| 7,034,552 | B2 * | 4/2006 | Kirchner et al. ............... 324/686 |
| 7,050,045 | B2 | 5/2006 | Baker et al. |
| 7,084,859 | B1 | 8/2006 | Pryor |
| 7,091,436 | B2 | 8/2006 | Serban |
| 7,091,998 | B2 | 8/2006 | Miller-Smith |
| 7,112,755 | B2 | 9/2006 | Kitano et al. |
| 7,113,179 | B2 | 9/2006 | Baker et al. |
| 7,154,484 | B2 | 12/2006 | Komata |
| 7,158,122 | B2 | 1/2007 | Roberts |
| 7,161,460 | B2 | 1/2007 | Federspiel |
| 7,170,428 | B2 | 1/2007 | Himberg et al. |
| 7,176,889 | B2 | 2/2007 | Baker et al. |
| 7,190,348 | B2 | 3/2007 | Kennedy et al. |
| 7,213,323 | B2 | 5/2007 | Baker et al. |
| 7,215,330 | B2 | 5/2007 | Rantet |
| 7,250,940 | B2 | 7/2007 | Jayanetti et al. |
| 7,295,904 | B2 | 11/2007 | Kanevsky et al. |
| 7,301,435 | B2 | 11/2007 | Lussey et al. |
| 7,310,089 | B2 | 12/2007 | Baker et al. |
| 7,324,095 | B2 | 1/2008 | Sharma |
| 7,336,260 | B2 | 2/2008 | Martin et al. |
| 7,345,675 | B1 | 3/2008 | Minakuchi |
| 7,356,769 | B2 | 4/2008 | Lehtonen |
| 7,377,133 | B2 | 5/2008 | Sandbach et al. |
| 7,388,571 | B2 | 6/2008 | Lowles et al. |
| 7,432,459 | B2 | 10/2008 | Stoschek et al. |
| 7,468,199 | B2 | 12/2008 | Divigalpitiya et al. |
| 7,511,702 | B2 | 3/2009 | Hotelling |
| 7,554,045 | B2 | 6/2009 | Sandbach et al. |
| 7,554,051 | B2 | 6/2009 | Crispin |
| 7,554,531 | B2 | 6/2009 | Baker et al. |
| 7,573,464 | B2 | 8/2009 | Baker et al. |
| 7,576,294 | B2 | 8/2009 | Clemens et al. |
| 7,603,917 | B2 | 10/2009 | Graham et al. |
| 7,614,008 | B2 | 11/2009 | Ording |
| 7,619,616 | B2 | 11/2009 | Rimas-Ribikauskas et al. |
| 7,629,966 | B2 | 12/2009 | Anson |
| 7,683,889 | B2 | 3/2010 | Rimas-Ribikauskas et al. |
| 7,683,890 | B2 | 3/2010 | Geaghan |
| 7,693,631 | B2 | 4/2010 | Yukawa et al. |
| 7,721,609 | B2 | 5/2010 | Wright |
| 7,724,242 | B2 | 5/2010 | Hillis et al. |
| 7,733,209 | B2 | 6/2010 | Kurtz |
| 7,746,327 | B2 | 6/2010 | Miyakoshi |
| 7,772,960 | B2 | 8/2010 | Baker |
| 7,773,075 | B2 | 8/2010 | Otsuka et al. |
| 7,777,730 | B2 | 8/2010 | Geurts et al. |
| 7,791,596 | B2 | 9/2010 | Errico et al. |
| 7,808,488 | B2 | 10/2010 | Martin et al. |
| 7,813,774 | B2 | 10/2010 | Perez-Noguera |
| 7,822,443 | B2 | 10/2010 | Kim et al. |
| 7,863,822 | B2 | 1/2011 | Stoschek et al. |
| 7,898,381 | B2 | 3/2011 | Hatsuda |
| 7,903,090 | B2 | 3/2011 | Soss et al. |
| 7,952,566 | B2 | 5/2011 | Poupyrev et al. |
| 7,973,773 | B2 | 7/2011 | Pryor |
| 8,022,933 | B2 | 9/2011 | Hardacker et al. |
| 8,026,902 | B2 | 9/2011 | Medler et al. |
| 8,026,906 | B2 | 9/2011 | Mölne |
| 8,035,535 | B2 | 10/2011 | Nousiainen |
| 8,037,770 | B2 | 10/2011 | Larson et al. |
| 8,049,730 | B2 | 11/2011 | Joguet et al. |
| 8,049,731 | B2 | 11/2011 | Baker et al. |
| 8,049,737 | B2 | 11/2011 | Cho et al. |
| 8,059,104 | B2 | 11/2011 | Shahoian et al. |
| 8,063,322 | B2 | 11/2011 | Katsurahira |
| 8,063,886 | B2 | 11/2011 | Serban et al. |
| 8,072,439 | B2 | 12/2011 | Hillis et al. |
| 8,072,440 | B2 | 12/2011 | Pryor |
| 8,081,165 | B2 | 12/2011 | Reiner |
| 8,082,029 | B2 * | 12/2011 | Honda ........................... 600/520 |
| 8,094,130 | B2 | 1/2012 | Griffin et al. |
| 8,095,278 | B2 | 1/2012 | Schaaf et al. |
| 8,098,236 | B2 | 1/2012 | Klein et al. |
| 8,113,065 | B2 | 2/2012 | Ohsato et al. |
| 8,120,586 | B2 | 2/2012 | Hsu et al. |
| 8,120,588 | B2 | 2/2012 | Klinghult |
| 8,130,207 | B2 | 3/2012 | Nurmi et al. |
| 8,134,535 | B2 | 3/2012 | Choi et al. |
| 8,139,038 | B2 | 3/2012 | Chueh et al. |
| 8,144,133 | B2 | 3/2012 | Wang et al. |
| 8,149,211 | B2 | 4/2012 | Hayakawa et al. |
| 8,151,210 | B2 | 4/2012 | Nezu et al. |
| 8,154,528 | B2 | 4/2012 | Chen et al. |
| 8,159,473 | B2 | 4/2012 | Cheng et al. |
| 8,169,295 | B2 | 5/2012 | Walkington |
| 8,171,431 | B2 | 5/2012 | Grossman et al. |
| 8,184,093 | B2 | 5/2012 | Tsuiki |
| 8,184,106 | B2 | 5/2012 | Serban |
| 8,188,985 | B2 | 5/2012 | Hillis et al. |
| 8,199,116 | B2 | 6/2012 | Jeon et al. |
| 8,212,790 | B2 | 7/2012 | Rimas-Ribikauskas et al. |
| 8,228,305 | B2 | 7/2012 | Pryor |
| 8,229,603 | B2 | 7/2012 | Miyata et al. |
| 8,237,537 | B2 | 8/2012 | Kurtz |
| 8,239,784 | B2 | 8/2012 | Hotelling et al. |
| 8,243,035 | B2 | 8/2012 | Abe et al. |
| 8,243,039 | B2 | 8/2012 | Trachte |
| 8,253,699 | B2 | 8/2012 | Son |
| 2001/0040551 | A1 | 11/2001 | Yates et al. |
| 2002/0097229 | A1 | 7/2002 | Rose et al. |
| 2002/0135457 | A1 | 9/2002 | Sandbach et al. |
| 2003/0011576 | A1 | 1/2003 | Sandbach et al. |
| 2003/0160808 | A1 | 8/2003 | Foote et al. |
| 2004/0071471 | A1 | 4/2004 | Baker et al. |
| 2004/0217331 | A1 | 11/2004 | Lussey et al. |
| 2004/0252007 | A1 | 12/2004 | Lussey et al. |
| 2005/0052427 | A1 | 3/2005 | Wu et al. |
| 2005/0239075 | A1 * | 10/2005 | Yanagidaira et al. ............. 435/6 |
| 2006/0025698 | A1 * | 2/2006 | Nakagawa et al. ........... 600/513 |

(56) References Cited

U.S. PATENT DOCUMENTS

| | | |
|---|---|---|
| 2006/0028454 A1 | 2/2006 | Branton et al. |
| 2006/0202954 A1 | 9/2006 | Ho |
| 2006/0255903 A1 | 11/2006 | Lussey et al. |
| 2007/0056493 A1 | 3/2007 | Burkitt et al. |
| 2007/0132736 A1 | 6/2007 | Crispin |
| 2007/0141939 A1 | 6/2007 | Sandbach et al. |
| 2007/0146313 A1 | 6/2007 | Newman et al. |
| 2007/0146342 A1 | 6/2007 | Medler et al. |
| 2007/0152959 A1 | 7/2007 | Peters |
| 2007/0176902 A1 | 8/2007 | Newman et al. |
| 2007/0229478 A1 | 10/2007 | Rosenberg et al. |
| 2007/0289859 A1 | 12/2007 | Sandbach et al. |
| 2008/0024438 A1 | 1/2008 | Collins et al. |
| 2008/0024454 A1 | 1/2008 | Everest |
| 2008/0030479 A1 | 2/2008 | Lowles et al. |
| 2008/0030482 A1 | 2/2008 | Elwell et al. |
| 2008/0036743 A1 | 2/2008 | Westerman et al. |
| 2008/0060854 A1 | 3/2008 | Perlin |
| 2008/0088577 A1 | 4/2008 | Lenneman et al. |
| 2008/0088600 A1 | 4/2008 | Prest et al. |
| 2008/0094367 A1 | 4/2008 | Van De Ven et al. |
| 2008/0170043 A1 | 7/2008 | Soss et al. |
| 2008/0211766 A1 | 9/2008 | Westerman et al. |
| 2008/0228046 A1* | 9/2008 | Futatsuyama et al. ........ 600/301 |
| 2008/0264183 A1 | 10/2008 | Graham et al. |
| 2008/0271933 A1 | 11/2008 | Morimoto |
| 2008/0278455 A1 | 11/2008 | Atkins et al. |
| 2008/0284743 A1 | 11/2008 | Hsu et al. |
| 2008/0289886 A1 | 11/2008 | Burkitt |
| 2008/0296073 A1 | 12/2008 | McDermid |
| 2008/0296140 A1 | 12/2008 | Yoshihara et al. |
| 2008/0302014 A1 | 12/2008 | Szczerba et al. |
| 2008/0303799 A1 | 12/2008 | Schwesig et al. |
| 2008/0303802 A1 | 12/2008 | Destura et al. |
| 2008/0309624 A1 | 12/2008 | Hotelling |
| 2008/0309626 A1 | 12/2008 | Westerman et al. |
| 2008/0316181 A1 | 12/2008 | Nurmi |
| 2009/0002325 A1 | 1/2009 | Jha et al. |
| 2009/0009482 A1 | 1/2009 | McDermid |
| 2009/0020343 A1 | 1/2009 | Rothkopf et al. |
| 2009/0027353 A1 | 1/2009 | Im et al. |
| 2009/0061823 A1 | 3/2009 | Chu |
| 2009/0095541 A1 | 4/2009 | Lee |
| 2009/0128507 A1 | 5/2009 | Hoshino et al. |
| 2009/0140985 A1 | 6/2009 | Liu |
| 2009/0140989 A1 | 6/2009 | Ahlgren |
| 2009/0153522 A1 | 6/2009 | Chou |
| 2009/0160793 A1 | 6/2009 | Rekimoto |
| 2009/0167722 A1 | 7/2009 | Villain |
| 2009/0184921 A1 | 7/2009 | Scott et al. |
| 2009/0201261 A1 | 8/2009 | Day |
| 2009/0237374 A1 | 9/2009 | Li et al. |
| 2009/0244017 A1 | 10/2009 | Pala et al. |
| 2009/0249191 A1 | 10/2009 | Leoutsarakos et al. |
| 2009/0256807 A1 | 10/2009 | Nurmi |
| 2009/0256817 A1 | 10/2009 | Perlin et al. |
| 2009/0258677 A1 | 10/2009 | Ellis et al. |
| 2009/0267921 A1 | 10/2009 | Pryor |
| 2009/0273573 A1 | 11/2009 | Hotelling |
| 2009/0279811 A1 | 11/2009 | Kilburn et al. |
| 2009/0309616 A1 | 12/2009 | Klinghult et al. |
| 2009/0322695 A1 | 12/2009 | Cho et al. |
| 2009/0327977 A1 | 12/2009 | Bachfischer et al. |
| 2010/0013774 A1 | 1/2010 | Chen et al. |
| 2010/0020030 A1 | 1/2010 | Kim et al. |
| 2010/0024573 A1 | 2/2010 | Daverman et al. |
| 2010/0026640 A1 | 2/2010 | Kim et al. |
| 2010/0039393 A1 | 2/2010 | Pratt et al. |
| 2010/0045624 A1 | 2/2010 | Hisatsugu et al. |
| 2010/0053078 A1 | 3/2010 | Kim et al. |
| 2010/0053116 A1 | 3/2010 | Daverman et al. |
| 2010/0062148 A1 | 3/2010 | Lussey et al. |
| 2010/0066697 A1 | 3/2010 | Jacomet et al. |
| 2010/0079391 A1 | 4/2010 | Joung |
| 2010/0079395 A1 | 4/2010 | Kim et al. |
| 2010/0085169 A1 | 4/2010 | Poupyrev et al. |
| 2010/0090973 A1 | 4/2010 | Algreatly |
| 2010/0097335 A1 | 4/2010 | Jung et al. |
| 2010/0097336 A1 | 4/2010 | Gomes et al. |
| 2010/0099394 A1 | 4/2010 | Hainzl |
| 2010/0102922 A1 | 4/2010 | Walkington |
| 2010/0110018 A1 | 5/2010 | Faubert et al. |
| 2010/0110026 A1 | 5/2010 | Kis et al. |
| 2010/0117978 A1 | 5/2010 | Shirado |
| 2010/0123667 A1 | 5/2010 | Kim et al. |
| 2010/0123678 A1 | 5/2010 | Kim et al. |
| 2010/0123686 A1 | 5/2010 | Klinghult et al. |
| 2010/0126840 A1 | 5/2010 | Walkington |
| 2010/0127975 A1 | 5/2010 | Jensen |
| 2010/0137702 A1* | 6/2010 | Park et al. ............... 600/393 |
| 2010/0141410 A1 | 6/2010 | Aono et al. |
| 2010/0153879 A1 | 6/2010 | Rimas-Ribikauskas et al. |
| 2010/0156818 A1 | 6/2010 | Burrough et al. |
| 2010/0171713 A1 | 7/2010 | Kwok et al. |
| 2010/0214239 A1 | 8/2010 | Wu |
| 2010/0222972 A1 | 9/2010 | Hustyi |
| 2010/0231540 A1 | 9/2010 | Cruz-Hernandez et al. |
| 2010/0250071 A1 | 9/2010 | Pala et al. |
| 2010/0253645 A1 | 10/2010 | Bolender |
| 2010/0265170 A1 | 10/2010 | Norieda |
| 2010/0271325 A1 | 10/2010 | Conte et al. |
| 2010/0277438 A1 | 11/2010 | Kawashima et al. |
| 2010/0283749 A1 | 11/2010 | Walkington |
| 2010/0308844 A1 | 12/2010 | Day et al. |
| 2010/0315349 A1 | 12/2010 | Choi |
| 2011/0006980 A1 | 1/2011 | Taniguchi et al. |
| 2011/0007023 A1 | 1/2011 | Abrahamsson et al. |
| 2011/0021251 A1 | 1/2011 | Lindén |
| 2011/0022393 A1 | 1/2011 | Wäller et al. |
| 2011/0030502 A1 | 2/2011 | Lathrop |
| 2011/0032203 A1 | 2/2011 | Pryor |
| 2011/0043468 A1 | 2/2011 | Lathrop et al. |
| 2011/0043491 A1 | 2/2011 | Oh |
| 2011/0050588 A1 | 3/2011 | Li et al. |
| 2011/0050589 A1 | 3/2011 | Yan et al. |
| 2011/0050591 A1 | 3/2011 | Kim et al. |
| 2011/0050629 A1 | 3/2011 | Homma et al. |
| 2011/0057899 A1 | 3/2011 | Sleeman et al. |
| 2011/0063248 A1 | 3/2011 | Yoon |
| 2011/0069024 A1 | 3/2011 | Kim |
| 2011/0074724 A1 | 3/2011 | Pryor |
| 2011/0082627 A1 | 4/2011 | Small et al. |
| 2011/0087983 A1 | 4/2011 | Shim |
| 2011/0107272 A1 | 5/2011 | Aguilar |
| 2011/0109578 A1 | 5/2011 | Wäller et al. |
| 2011/0115736 A1 | 5/2011 | Joguet et al. |
| 2011/0128164 A1 | 6/2011 | Kang et al. |
| 2011/0128235 A1 | 6/2011 | Rogers et al. |
| 2011/0128250 A1 | 6/2011 | Murphy et al. |
| 2011/0141052 A1 | 6/2011 | Bernstein et al. |
| 2011/0141053 A1 | 6/2011 | Bulea et al. |
| 2011/0175754 A1 | 7/2011 | Karpinsky |
| 2011/0175844 A1 | 7/2011 | Berggren |
| 2011/0175845 A1 | 7/2011 | Honda et al. |
| 2011/0181430 A1 | 7/2011 | Hu et al. |
| 2011/0181546 A1 | 7/2011 | Joguet et al. |
| 2011/0187674 A1 | 8/2011 | Baker et al. |
| 2011/0193813 A1 | 8/2011 | Gralewski et al. |
| 2011/0205151 A1 | 8/2011 | Newton et al. |
| 2011/0205162 A1 | 8/2011 | Wäller et al. |
| 2011/0205182 A1 | 8/2011 | Miyazawa et al. |
| 2011/0210926 A1 | 9/2011 | Pasquero et al. |
| 2011/0221564 A1 | 9/2011 | Deppiesse et al. |
| 2011/0221684 A1 | 9/2011 | Rydenhag |
| 2011/0221693 A1 | 9/2011 | Miyazaki |
| 2011/0221694 A1 | 9/2011 | Karaoguz et al. |
| 2011/0227870 A1 | 9/2011 | Kim |
| 2011/0227872 A1 | 9/2011 | Huska et al. |
| 2011/0239110 A1 | 9/2011 | Garrett et al. |
| 2011/0242029 A1 | 10/2011 | Kasahara et al. |
| 2011/0248942 A1 | 10/2011 | Yana et al. |
| 2011/0253948 A1 | 10/2011 | Lussey et al. |
| 2011/0260965 A1 | 10/2011 | Kim et al. |
| 2011/0267294 A1 | 11/2011 | Kildal |

(56) References Cited

U.S. PATENT DOCUMENTS

| | | |
|---|---|---|
| 2011/0273394 A1 | 11/2011 | Young et al. |
| 2011/0275412 A1 | 11/2011 | Khawand |
| 2011/0278078 A1 | 11/2011 | Schediwy et al. |
| 2011/0304559 A1 | 12/2011 | Pasquero |
| 2011/0304581 A1 | 12/2011 | An et al. |
| 2011/0316811 A1 | 12/2011 | Kitagawa |
| 2012/0001870 A1 | 1/2012 | Lee et al. |
| 2012/0019448 A1 | 1/2012 | Pitkanen et al. |
| 2012/0019463 A1 | 1/2012 | Ng et al. |
| 2012/0026124 A1 | 2/2012 | Li et al. |
| 2012/0032899 A1 | 2/2012 | Waeller et al. |
| 2012/0032907 A1 | 2/2012 | Koizumi et al. |
| 2012/0032915 A1 | 2/2012 | Wittorf |
| 2012/0044169 A1 | 2/2012 | Enami |
| 2012/0044172 A1 | 2/2012 | Ohki et al. |
| 2012/0050159 A1 | 3/2012 | Yu et al. |
| 2012/0050208 A1 | 3/2012 | Dietz |
| 2012/0056818 A1 | 3/2012 | Shafi et al. |
| 2012/0056837 A1 | 3/2012 | Park et al. |
| 2012/0062603 A1 | 3/2012 | Mizunuma et al. |
| 2012/0068946 A1 | 3/2012 | Tang et al. |
| 2012/0068965 A1 | 3/2012 | Wada et al. |
| 2012/0068969 A1 | 3/2012 | Bogana et al. |
| 2012/0081327 A1 | 4/2012 | Heubel et al. |
| 2012/0086659 A1 | 4/2012 | Perlin et al. |
| 2012/0086670 A1 | 4/2012 | Teil et al. |
| 2012/0092250 A1 | 4/2012 | Hadas et al. |
| 2012/0092279 A1 | 4/2012 | Martin |
| 2012/0092294 A1 | 4/2012 | Ganapathi et al. |
| 2012/0092299 A1 | 4/2012 | Harada et al. |
| 2012/0092324 A1 | 4/2012 | Buchan et al. |
| 2012/0105358 A1 | 5/2012 | Momeyer et al. |
| 2012/0105367 A1 | 5/2012 | Son et al. |
| 2012/0113028 A1 | 5/2012 | Marsden et al. |
| 2012/0113054 A1 | 5/2012 | Hashimoto et al. |
| 2012/0113061 A1 | 5/2012 | Ikeda |
| 2012/0120009 A1 | 5/2012 | Lussey et al. |
| 2012/0127088 A1 | 5/2012 | Pance et al. |
| 2012/0127107 A1 | 5/2012 | Miyashita et al. |
| 2012/0127179 A1 | 5/2012 | Aspelin |
| 2012/0139864 A1 | 6/2012 | Sleeman et al. |
| 2012/0146945 A1 | 6/2012 | Miyazawa et al. |
| 2012/0147052 A1 | 6/2012 | Homma et al. |
| 2012/0154315 A1 | 6/2012 | Aono |
| 2012/0154316 A1 | 6/2012 | Kono |
| 2012/0154317 A1 | 6/2012 | Aono |
| 2012/0154318 A1 | 6/2012 | Aono |
| 2012/0154328 A1 | 6/2012 | Kono |
| 2012/0154329 A1 | 6/2012 | Shinozaki |
| 2012/0154330 A1 | 6/2012 | Shimizu |
| 2012/0162122 A1 | 6/2012 | Geaghan |
| 2012/0169609 A1 | 7/2012 | Britton |
| 2012/0169617 A1 | 7/2012 | Mäenpää |
| 2012/0169635 A1 | 7/2012 | Liu |
| 2012/0169636 A1 | 7/2012 | Liu |
| 2012/0188181 A1 | 7/2012 | Ha et al. |
| 2012/0194460 A1 | 8/2012 | Kuwabara et al. |
| 2012/0194466 A1 | 8/2012 | Posamentier |
| 2012/0204653 A1 | 8/2012 | August et al. |
| 2012/0205165 A1 | 8/2012 | Strittmatter et al. |
| 2012/0206393 A1 | 8/2012 | Hillis et al. |
| 2012/0218212 A1 | 8/2012 | Yu et al. |

FOREIGN PATENT DOCUMENTS

| | | |
|---|---|---|
| DE | 60130983 T2 | 7/2008 |
| EP | 1887595 A1 | 2/2008 |
| GB | 2423646 A | 8/2006 |
| GB | 2445505 A | 7/2008 |
| GB | 2448893 A | 11/2008 |
| GB | 2450587 A | 12/2008 |
| GB | 2452714 A | 3/2009 |
| GB | 2454619 A | 5/2009 |
| GB | 2462920 A | 3/2010 |
| GB | 2465077 A | 5/2010 |
| GB | 2465713 A | 6/2010 |
| GB | 2468870 A | 9/2010 |
| GB | 2437997 B | 7/2011 |
| GB | 2443658 B | 9/2011 |
| WO | 9803193 A1 | 7/1998 |
| WO | 9938173 A1 | 7/1999 |
| WO | 0079546 A1 | 12/2000 |
| WO | 0188935 A1 | 11/2001 |
| WO | 02099822 A2 | 12/2002 |
| WO | 2005029514 A1 | 3/2005 |
| WO | 2006016138 A1 | 2/2006 |
| WO | 2008135787 A1 | 11/2008 |
| WO | 2009034313 A2 | 3/2009 |
| WO | 2010023449 A1 | 3/2010 |
| WO | 2010109186 A2 | 9/2010 |

\* cited by examiner

STEERING WHEEL WITH HAND SENSORS

This application claims priority to and the benefit of U.S. Provisional Patent Application No. 61/320,591, filed Apr. 2, 2010, incorporated by reference herein in its entirety.

BACKGROUND

The present disclosure generally relates to the field of vehicle sensors. More specifically, the disclosure relates to a biological parameter sensor coupled to a vehicle steering wheel.

Conventional steering wheels do not have the capability of measuring parameters that may give an indication of the driver's well being. Such parameters can include, for example, heart rate, skin capacitance, skin temperature, respiration rate, and other parameters utilized to determine a driver's well being or condition.

It would be desirable to provide a method and mechanism to evaluate and measure the driver's well being. In addition, it would be desirable to provide such a mechanism as a cost effective device which can be integrated into vehicle designs.

SUMMARY

According to an embodiment, a steering wheel for a vehicle can include a sensor assembly mounted in the steering wheel. The sensor assembly can include an electrode configured to measure a biological parameter of a driver of the vehicle.

A sensor assembly for a steering wheel can include an electrode configured to measure a biological parameter of a driver of the vehicle. The sensor assembly can be configured to be mounted in the steering wheel.

BRIEF DESCRIPTION OF THE DRAWINGS

These and other features, aspects, and advantages of the present embodiments will become apparent from the following description, appended claims, and the accompanying exemplary embodiments shown in the drawings, which are briefly described below.

DETAILED DESCRIPTION

Figure 1:
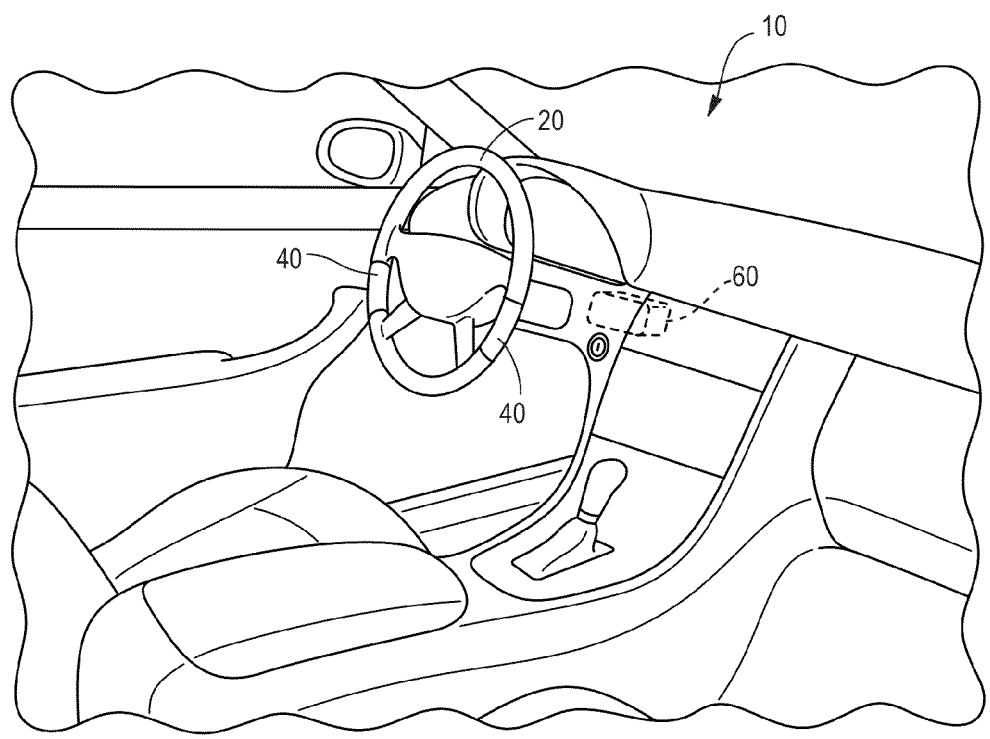
FIG. 1 is an isometric view of a vehicle cockpit interior, showing a steering wheel with sensor assemblies, according to an example.

FIG. 1 shows an example of a cockpit interior 10 for a vehicle which includes a steering wheel 20. As is normally done in driving a vehicle, a driver may rotate the steering wheel 20 to turn the wheels of the vehicle and steer the vehicle in a desired direction.

Such a steering wheel 20 may include various controls in the form of switches or buttons provided within easy reach of the driver. For example, such controls could be used to actuate a vehicle audio system (e.g., volume, tuning, mode, etc.), to control vehicle lighting (e.g., overhead lighting, headlights, etc.), to control a phone, or to control other features or devices, such as cruise control. Such controls, including controls for systems including an audio system, climate system, lighting system or other systems, may additionally be provided elsewhere in the vehicle, such as on the vehicle dash or center console of the vehicle.

Figure 2:
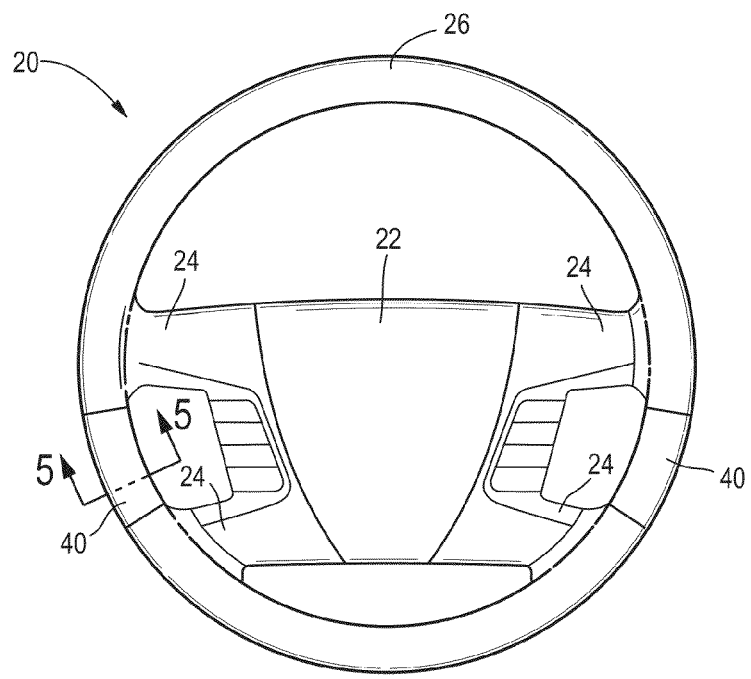
FIG. 2 is a front view of a steering wheel with sensor assemblies, according to an example.

As shown in the example of FIG. 2, the steering wheel 20 can include a central hub 22 which is connected to an outer ring or rim 26 by one or more spokes 24. The hub 22 can in turn be coupled to a steering column of the vehicle 10. As is normally done when driving a vehicle, a driver can turn the steering wheel 12 by grasping the outer rim 26.

The steering wheel 20 may be a four-spoke steering wheel, as shown in the example of FIG. 2. In another example, the steering wheel 20 may be a three-spoke steering wheel. In other examples, the steering wheel 20 may have a different number or arrangement of spokes.

As shown in the examples FIG. 1 and FIG. 2, the steering wheel 20 can include sensor assemblies 40. For example, the outer rim 26 of the steering wheel 20 can include a pair of sensor assemblies 40 that are integrated into the outer rim 26. The sensor assemblies 40 can be capable of measuring parameters that may give an indication of the driver's well being. Such parameters can include, for example, heart rate, skin capacitance, skin temperature, respiration rate, and other biological parameters. The sensor assemblies 40 are configured to be relatively unobtrusive, both tactilely and visually, so that the sensor assemblies are integrated into a steering wheel, such as the outer rim 26 of a steering wheel 20.

Figure 3:
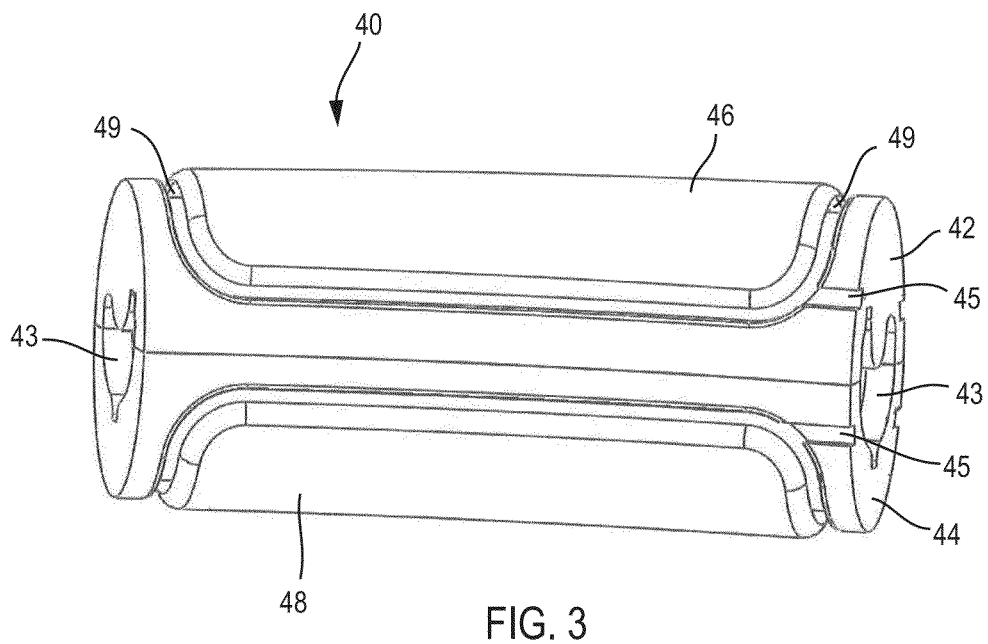
FIG. 3 is a perspective view of a sensor assembly for a steering wheel showing a side of a sensor assembly along the inner diameter of the steering wheel, according to an example.

FIG. 3 shows an example of a sensor assembly 40. The sensor assembly 40 can include a main body or housing, such as a housing formed from an upper housing 42 and a lower housing 44, as shown in the example of FIG. 3. Such upper and lower housings can be coupled together with snap and location features which engage each other from both sides of a steering wheel armature. The upper housing 42 and the lower housing 44 can be coupled together at an interlock portion 41, such as a tongue and groove interlock (shown best in the example of FIG. 5) which may include snap and location features to properly align and secure the upper housing 42 to the lower housing 44. The upper housing 42 and the lower housing 44 can be curved to match the radius of curvature of the outer rim 26. When coupled together, the upper housing 42 and the lower housing 44 may define a central void or cavity 43 which can receive an armature 30 of the outer rim 26.

Hollow portions of the inner cavity 43 of the housing, which can be a volume that is not occupied by the armature 30 or other portions of the outer rim 26, may be selectively filled with a material, such as a polyurethane foam, to aid in securing and locating a sensor assembly 40 to the steering wheel 20 and to provide comfort to a driver grasping the steering wheel 20. Such polyurethane foam or other suitable materials may also be used to dampen vibrations or other noise.

The upper housing 42 and the lower housing 44 can be formed, for example, from a non-conductive material, such as, for example, a polymer, wood, or a composite material such as a fiber reinforced polymer, to electrically isolate the electrodes of a sensor assembly. In another example, the upper housing 42 and/or the lower housing 44 may be formed from a conductive material and an insulator may be provided either between the electrodes and the housings 42 and 44, or at the interlock 41 where the upper housing 42 is coupled to the lower housing 44.

The upper housing 42 and the lower housing 44 provide various features to allow a sensor assembly 40 to be integrated unobtrusively into a steering wheel 20, such as the outer rim 26 of a steering wheel 20. The sensor assembly 40 can therefore be a structure for mounting the sensor components, allow the wiring for sensors of the sensor assembly to be self contained in the unit, and allow the unit to be seamlessly integrated into a steering wheel, such as a leather-covered steering wheel, at low cost.

A sensor assembly 40 can include an upper electrode 46 and a lower electrode 48. Such upper and lower electrodes 46, 48 can be mounted on opposite sides of the sensor assembly 40. as shown in the example of FIG. 3. The pair of electrodes 46, 48 can be provided on each of the sensor assemblies 40 so that each of driver's hands grasp the pair of electrodes 46, 48, such as by grasping both of the electrodes 46, 48 at once. The housings of a sensor assembly 40 can provide a structure for mounting sensor components, allow wiring for the electrodes 46, 48 to be self contained, and permit the unit to be seamlessly integrated into a steering wheel, including leather steering wheels.

The electrodes 46 and 48 can be coupled to an outer surface of the housings 42 and 44 (which faces the interior of the vehicle and a driver of the vehicle), such as with snap features. In another example, the electrodes 46 and 48 can be coupled to the housings 42 and 44 via other methods, such as mechanical fasteners, adhesives, etc.

Figure 4:
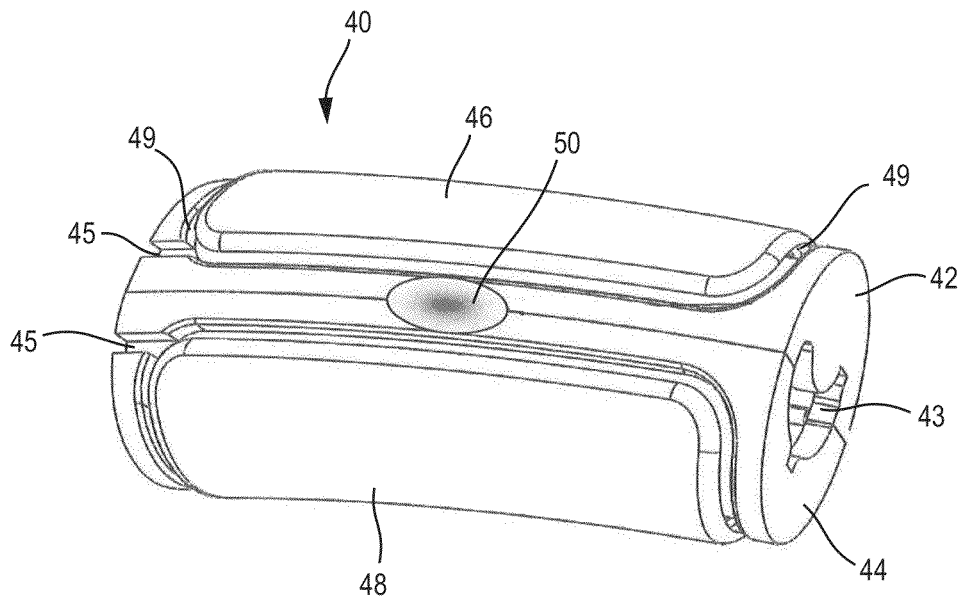
FIG. 4 is a perspective view of a sensor assembly for a steering wheel showing a side of a sensor assembly along the outer periphery of the steering wheel, according to an example.

Wires or other conductive members (not shown in the drawings) can be coupled to the back sides of the electrodes 46 and 48 (e.g., the sides adjacent to and facing the housings 42 and 44). The wires may then pass through grooves 45 formed in a surface of the upper housing 42 and/or the lower housing 44, as shown in the examples of FIG. 3 and FIG. 4. Such wire grooves 45 can be in the form of, for example, troughs, depressions, or slots. The wire grooves 45 allow the wires to remain recessed so that the wires and other features of the sensor assembly does not interfere with the relatively smooth and featureless contour of the sensor assemblies, thereby allowing them to be better integrated into a steering wheel 20, such as the outer rim 26 of the steering wheel 20. In addition, the sensory assemblies 40 provide a low cost unit which includes sensors and connections, such as wiring, which can be more easily integrated into a steering wheel. By providing the sensory assemblies 40 with such a smooth and featureless contour, the sensory assemblies 40 can be provided as a modular unit which can be integrated into existing vehicles at low cost.

In another example, the sensor assembly 40 may not include an upper housing 42 and lower housing 44 and the electrodes of the sensory assembly 40 may be directly coupled to or formed on the outer rim 26 of the steering wheel 20. For example, the electrodes 46 and 48 may be integrated into a polyurethane foam surrounding the armature 30. In another exemplary embodiment, the electrodes 46 and 48 may be a flexible body such as an electrically conductive fabric that is sewn or otherwise coupled to a skin 32 of the steering wheel 20. In any exemplary embodiment, the electrodes 46 and 48 and the surrounding components are arranged such that the upper electrode 46 is isolated from the lower electrode 28 so that an electrical current is not able to flow directly between the electrodes 46 and 48.

According to an example, the upper electrode 46 and the lower electrode 48 are formed at least partially of a conductive material with low resistance. For example, the upper electrode 46 and the lower electrode 48 can have a conductive surface formed by a chrome plating, metal wrap, metal paint, or a metalized fabric or metalized leather. In other examples, metalized fabrics and leathers could be used for the upper electrode 46 and lower electrode 48. Stainless steels can also be used for the electrodes, according to another example.

The electrodes 46, 48 can be curved to match a radius of curvature of the outer rim 26 and, when the electrodes 46, 48 are assembled with the upper housing 42 and the lower housing 44, the electrodes 46, 48 can form a diameter for the sensor assembly 40 that is substantially equal to the diameter and shape of a cross section of the outer rim 26. The electrodes are preferably formed of a conductive material with low resistance, and are isolated from one another.

The finish and color of the conductive surfaces of the upper electrode 46 and lower electrode 48 may be chosen to match with the aesthetic requirements of a vehicle. For example, the surfaces of the electrodes 46, 48 can be designed and selected to match or compliment other trim components in the interior of a vehicle interior.

The covering or skin 32 is configured to provide an aesthetically pleasing exterior for the steering wheel 20. The skin 32 is also configured to add an ergonomically pleasing layer to the outside of the steering wheel 20 to improve the comfort of the driver. According to an example, the skin 32 may be formed from an injection molded polyurethane material. According to other examples, the skin 32 may be formed from a wide variety of other molded materials such as olefinic thermoplastic elastomers (TEOs), thermoplastic olefins (TPOs), rubber, or any other suitable material. According to other examples, the skin 32 may be a film or sheet that is wrapped around the armature, such as leather, fabric, a polymer material. In another example, the skin 32 may be a shell of laminate formed from a generally rigid material such as wood, a carbon fiber composite, etc. An underlay material such as a foam may be provided under the skin 32 to further increase the ergonomic comfort of the driver.

The covering or skin 32 of the steering wheel 20 can be wrapped around the upper housing 42 and lower housing 44. The covering or skin 32 can be, for example, leather, TPO, and other coverings used in the art. The covering 32 can include openings which allow the electrodes 46 and 48 to protrude through the covering 32 so that the electrodes 46, 48 may contact the hands of the driver which grip the steering wheel 20. For example, the skin 32 can be wrapped around the housing of a sensor assembly and be secured in place by glue so that the electrodes would sit atop of the skin 32.

The surfaces of the electrodes 46, 48 can be flush with the surface of the skin 32 such that they form a generally continuous surface and are not uncomfortable for the driver when grasping the steering wheel 20. As a result, the sensor assembly does not interfere with the relatively smooth and featureless contour of the sensor assemblies, thereby allowing the assembly to be better integrated into a steering wheel of a vehicle at low cost.

Figure 5:
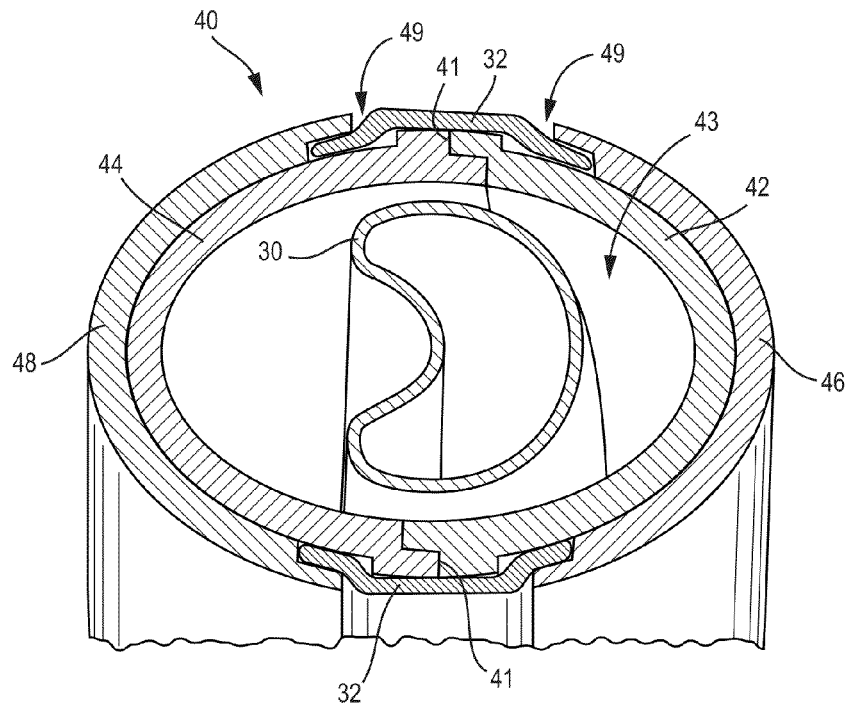
FIG. 5 is a cross section of the sensor assembly of FIG. 3, according to an example.

The edges of the skin 32 may be received by grooves 49 around a periphery of the electrodes 46 and 48, as shown in the examples of FIG. 3, FIG. 4, and FIG. 5. Such grooves 49 can be, for example, slots, voids, depressions, or cavities provided by edges of the electrodes or formed in a surface of the housing, such as housings 42, 44. When the electrodes 46 and 48 are coupled to the housings 42 and 44, the edges of the skin 32 may be trapped or compressed in the grooves 49, thus securing the skin 32 to the sensor assemblies 40 and to the steering wheel 20, such as an armature 30 of the steering wheel 20. In this manner, the skin may be tucked underneath the electrodes, as shown in the examples of FIG. 5 or the skin might not be tucked underneath the electrodes, such as by tucking the skin into a groove 49 formed in a surface of the housing. According to another example, the skin 32 may by further secured with the use of other fastening means, such as adhesives, stitching, and other covering or skin fastening means used in the art.

The outer rim 26 of the steering wheel 20 can include an armature 30, as shown in the example of FIG. 5. The armature 30 can be formed from a rigid material such as a metal (e.g., steel, magnesium, or aluminum, etc.), a polymer, wood, or a composite material such as a reinforced polymer (e.g., a fiber-reinforced polymer, a particle reinforced polymer, etc.). Such an armature 30 can be provided in the form of, for example, a frame, shell, base, or other forms used in the art.

The armature 30 can provide strength and shape to a steering wheel 20. If the armature 30 is a hollow body, it may be filled with a sound-dampening material, such as a polyurethane foam or other suitable material. The armature 30 may be surrounded by another material that makes up the main body of the outer rim 26 such as a polymer, foam, wood, etc. The armature 30 may be covered with the skin 32 which at least partially covers the armature 30. The steering wheel 20 may have further components coupled to it such as appliqués formed from materials (such as leather or wood), separate back covers, switches, bezels, etc.

According to an example, the electrodes 46, 48 can be used to measure various biological parameters, such as the heart rate of the driver and the skin capacitance of the driver's hands.

The heart rate of a driver who grips the steering wheel with his or her hands can be sensed by the sensor assemblies. For example, sensor assemblies 40 can be mounted on the left and right sides of a steering wheel such that two electrodes (such as the upper and a lower electrodes 46, 48) are provided for each hand on opposite sides of the steering wheel.

In another example, the upper left hand and upper right hand electrodes and lower left hand and lower right hand electrodes of sensor assemblies positioned on the left hand and right hand sides of a steering wheel can be connected and data recorded from the electrodes can be compared to determine the heart rate response of the driver. For example, wires can be used to couple together the upper electrodes 46 of the two sensor assemblies 40 and to couple together the lower electrodes 48 of the two sensor assemblies 40. Thus, simply by a driver grasping the steering wheel with his or her hands while operating a vehicle, the electrodes 46, 48 of sensor assemblies mounted in the steering wheel can measure the heart rate and other biological parameters of a driver to determine the well being of the driver.

Skin capacitance can be measured by monitoring the conductance between the upper and lower electrodes of a sensor assembly. The skin capacitance can be measured to indicate the degree or amount of sweat on the driver's hands or the galvanic skin response, which would in turn affect the conductance measured by the electrodes of a sensor assembly. For example, the skin capacitance can be measured by sensor assemblies on the left and right sides of a steering wheel and the results averaged to provide a skin capacitance.

Figure 6:
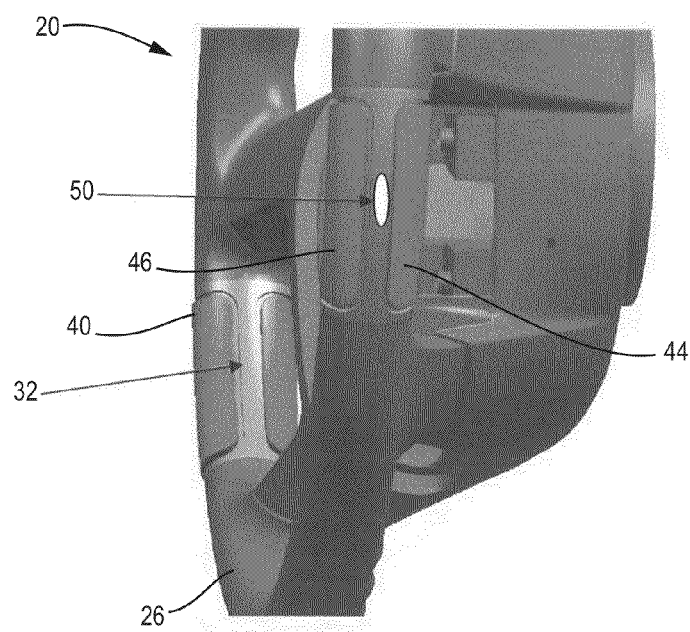
FIG. 6 is a side view of a steering wheel having a sensor assembly which includes a temperature sensor, according to an example.

Skin temperature can be measured using a temperature sensor included in a sensor assembly. A temperature sensor can be, for example, an infrared (IR) sensor mounted in the steering wheel, such as the rim of the steering wheel. For example, a temperature sensor 50 can be contained within the housing of a sensor assembly 40, as shown in the examples of FIG. 4 and FIG. 6. Such a temperature sensor 50 can be located on an exterior part of a steering wheel rim between the electrodes 46, 48 of a sensor assembly 40, such that the temperature sensor contacts the skin of a driver or is close to the skin of a driver. The temperature of a driver's skin can be measured at the same time as measuring the heart rate and/or skin capacitance values via the electrodes of one or more sensor assemblies 40. By placing the temperature sensor 50 along the outer periphery of the outer rim 26 of a steering wheel, for example, it is more likely to have contact with the surface of the hand (e.g., the palm) or be in close proximity thereto. For example, the temperature sensor should positioned to preferably be within 1-3 inches of a hand contacting the steering wheel. The temperature sensor 50 may be coupled to the electrodes 46 and 48 or to other components such as the signal processing unit 60 through wires or other conductive paths that are recessed or concealed in the bodies of the upper housing 42 and/or the lower housing 44.

The temperature sensor 50 of a sensor assembly 40 may be surrounded by the skin or cover 32, such as the leather or exterior garnish element of a steering wheel, and the sensor wired to a rear side of the sensor. A surface of the temperature sensor 50 can be flush with the surface of the skin or covering 32 such that the temperature sensor 50 is not tactilely noticeable by the driver and the smooth surface of the sensor assembly 40 is maintained so that the sensor assembly 40 may be easily integrated into a steering wheel.

The sensor assemblies 40, including the electrodes 46 and 48 of sensor assemblies, can be connected to a signal processing unit 60 in a vehicle. Such a signal processing unit 60 may be disposed elsewhere in the vehicle, such as in the vehicle dash, as shown in the example of FIG. 1. When the driver places both hands on the steering wheel 20, such that driver's hands contact the electrodes 46 and 48 on each of the two sensor assemblies 40, the driver's heart rate can be measured by monitoring the driver's electrocardiography (EKG) signal using the electrodes 46 and 48 of one or more sensor assemblies and the signal processing unit 60. In another example, skin capacitance (e.g., sweatiness) can be measured by monitoring the conductance between the upper electrodes 46 and the lower electrodes 48 for the left side and right side sensor assemblies 40 and averaging the results with the signal processing unit 60. The signal processing unit 60 can also be used to process signals from a temperature sensor 50 and to process the signals from one or more sensors of one or more sensor assemblies 40, such as heart rate and/or skin capacitance signals from the electrodes 46, 48 and/or the temperature sensor 50.

The measured heart rate and/or the skin capacitance calculated by the signal processing unit 60 may be stored, transmitted to a remote or local database, and/or may be displayed for the driver, such as on a monitor or display on the vehicle dash or on a heads-up display.

Measured biological parameters of a driver, such as the heart rate, skin capacitance, and/or skin temperature, can be used by a vehicle controller, such as the signal processing unit 60 or other CPU, to determine if a driver of a vehicle is in a stressed state or is otherwise distressed. For example, the vehicle could determine that although the temperature of the vehicle interior is at a comfortable level the skin of the driver is sweaty, the heart rate for the driver is at a relatively high level, or that the skin temperature of the driver is abnormally high. Such information could then be used, for example, to alter the vehicle environment, such as by the air conditioning or the lighting of the vehicle to affect the stress level of the driver, or to inquire whether the driver is in satisfactory condition, such as by an automated inquiring or by connecting to a remote service, such as a cell phone based vehicle customer service.

While the sensor assembly is discussed in general as being integrated into the outer rim 26 of a steering wheel, in other embodiments, the novel features of the sensor assembly 40 may be used to integrate the sensor assembly 40 into other portions of the steering wheel 20, such as, for example, in the spokes 24 or the hub 22 of a steering wheel. All or some of the above sensing elements can be packaged in one unit or sensor assembly. The sensor assembly can provide features such as wire channels, leather tuck, and finish grooves for the seamless integration with the rest of the steering wheel so that the sensor assembly has a tactilely smooth surface.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

The terms "coupled," "connected," and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

References herein to the positions of elements (e.g., "upper," "lower," "above," "below," etc.) are merely used to describe the orientation of various elements in the FIGURES. It should be noted that the orientation of various elements may differ according to other exemplary embodiments, and that such variations are intended to be encompassed by the present disclosure.

It is important to note that the construction and arrangement of a steering wheel with hand sensors and method of monitoring a driver as shown in the various exemplary embodiments is illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. For example, elements shown as integrally formed may be constructed of multiple parts or elements, the position of elements may be reversed or otherwise varied, and the nature or number of discrete elements or positions may be altered or varied. The order or sequence of any process or method steps may be varied or re-sequenced according to alternative embodiments. Other substitutions, modifications, changes and omissions may also be made in the design, operating conditions and arrangement of the various exemplary embodiments without departing from the scope of the present embodiments.

What is claimed is:

1. A steering wheel for a vehicle, comprising:
    a sensor assembly mounted in the steering wheel, wherein the sensor assembly includes a pair of electrodes configured to measure a biological parameter of a driver of the vehicle due to contact with one hand of the driver, wherein the pair of electrodes are electrically isolated from one another such that an electrical current cannot flow directly between the pair of electrodes; and
    a temperature sensor configured to measure a skin temperature of the driver and disposed on an outer periphery of the steering wheel between the pair of electrodes.

2. The steering wheel of claim 1, wherein the sensor assembly is mounted in a rim of the steering wheel.

3. The steering wheel of claim 1, further comprising a steering wheel covering, wherein a surface of the steering wheel covering and surfaces of the pair of electrodes are substantially flush with one another so that the steering wheel has a tactilely smooth surface.

4. The steering wheel of claim 1, wherein the sensor assembly is configured to measure the heart rate of a driver.

5. The steering wheel of claim 1, wherein the sensor assembly is configured to measure the skin capacitance of a driver.

6. The steering wheel of claim 1, wherein the temperature sensor is positioned to be within 1-3 inches of a driver's hand contacting the steering wheel.

7. The steering wheel of claim 1, wherein the pair of electrodes are separated from one another so that surfaces of the electrodes are not in contact with one another.

8. The steering wheel of claim 1, wherein the sensor assembly includes a housing, wherein the housing is formed in two pieces.

9. The steering wheel of claim 8, further comprising a steering wheel armature, wherein the two pieces of the housing are fitted around the armature of the steering wheel.

10. The steering wheel of claim 8, wherein the two housing pieces interlock via a tongue and groove.

11. The steering wheel of claim 1, wherein the temperature sensor includes an infrared temperature sensor.

12. A vehicle, comprising:
    a frame;
    a cockpit interior supported, at least partially, by the frame;
    a steering wheel disposed proximate to the cockpit interior and configured, when rotated, to steer the vehicle in a desired direction, the steering wheel including:
        a sensor assembly mounted in the steering wheel and electrically coupled to a vehicle controller, wherein the sensor assembly includes a pair of electrodes configured to measure a biological parameter of a driver of the vehicle due to contact with one hand of the driver, wherein the pair of electrodes are electrically isolated from one another such that an electrical current cannot flow directly between the pair of electrodes; and
        a temperature sensor configured to measure a skin temperature of the driver and disposed on an outer periphery of the steering wheel between the pair of electrodes;
    wherein the vehicle controller is configured to alter at least one aspect of a vehicle environment based on at least one of the biological parameter or skin temperature of the driver.

13. The vehicle of claim 12, wherein altering at least one aspect of a vehicle environment includes adjusting a parameter associated with an air conditioning system of the vehicle.

14. The vehicle of claim 12, wherein altering at least one aspect of a vehicle environment includes adjusting a lighting level of the vehicle.

15. The vehicle of claim 12, wherein the sensor assembly is configured to measure the heart rate of a driver.

16. The vehicle of claim 12, wherein the sensor assembly is configured to measure the skin capacitance of a driver.

17. The vehicle of claim 12, wherein the temperature sensor is positioned to be within 1-3 inches of a driver's hand contacting the steering wheel.

18. The vehicle of claim 12, wherein the pair of electrodes are separated from one another so that surfaces of the electrodes are not in contact with one another.

19. The vehicle of claim 12, wherein the sensor assembly includes a housing, wherein the housing is formed in two pieces.

20. The vehicle of claim 12, wherein the temperature sensor includes an infrared temperature sensor.

* * * * *